United States Patent [19]

Shekarriz et al.

[11] Patent Number: 6,067,861
[45] Date of Patent: May 30, 2000

[54] METHOD AND APPARATUS FOR ULTRASONIC DOPPLER VELOCIMETRY USING SPEED OF SOUND AND REFLECTION MODE PULSED WIDEBAND DOPPLER

[75] Inventors: Alireza Shekarriz, Kennewick; David M. Sheen, Richland, both of Wash.

[73] Assignee: Battelle Memorial Institute, Richland, Wash.

[21] Appl. No.: 09/100,293

[22] Filed: Jun. 18, 1998

[51] Int. Cl.[7] .......................................... G01F 1/66
[52] U.S. Cl. ...................... 73/861.25; 73/861.27; 73/597; 600/455; 367/89
[58] Field of Search ................. 73/861.27, 861.25, 73/861.26, 861.28, 861.29, 861.31, 861.18, 861.05, 861.04, 861, 597; 600/455, 456, 454; 367/89, 90

[56] References Cited

U.S. PATENT DOCUMENTS

| | | | |
|---|---|---|---|
| 4,176,337 | 11/1979 | Aechter et al. | 367/131 |
| 4,993,418 | 2/1991 | Weaver et al. | 128/661.08 |
| 5,113,867 | 5/1992 | Janszen | 128/661.09 |
| 5,115,670 | 5/1992 | Shen | 73/61.41 |
| 5,226,328 | 7/1993 | Petroff et al. | 73/861.25 |
| 5,341,809 | 8/1994 | Katakura | 128/661.09 |
| 5,363,848 | 11/1994 | Spani et al. | 128/661.09 |
| 5,463,906 | 11/1995 | Spani et al. | 73/861.27 |
| 5,473,948 | 12/1995 | Moss et al. | 73/861.25 |
| 5,521,883 | 5/1996 | Fage et al. | 367/90 |
| 5,835,884 | 11/1998 | Brown | 702/45 |
| 5,844,144 | 12/1998 | Jennings | 73/861.25 |

*Primary Examiner*—Benjamin R. Fuller
*Assistant Examiner*—Jagdish Patel
*Attorney, Agent, or Firm*—Paul W. Zimmerman

[57] ABSTRACT

According to the present invention, a method and apparatus rely upon tomographic measurement of the speed of sound and fluid velocity in a pipe. The invention provides a more accurate profile of velocity within flow fields where the speed of sound varies within the cross-section of the pipe. This profile is obtained by reconstruction of the velocity profile from the local speed of sound measurement simultaneously with the flow velocity. The method of the present invention is real-time tomographic ultrasonic Doppler velocimetry utilizing a to plurality of ultrasonic transmission and reflection measurements along two orthogonal sets of parallel acoustic lines-of-sight. The fluid velocity profile and the acoustic velocity profile are determined by iteration between determining a fluid velocity profile and measuring local acoustic velocity until convergence is reached.

8 Claims, 17 Drawing Sheets

METHOD AND APPARATUS FOR ULTRASONIC DOPPLER VELOCIMETRY USING SPEED OF SOUND AND REFLECTION MODE PULSED WIDEBAND DOPPLER

This invention was made with Government support under Contract DE-AC0676RLO1830 awarded by the U.S. Department of Energy. The Government has certain rights in the invention.

FIELD OF THE INVENTION

The invention is an ultrasonic method and apparatus for measuring a velocity profile of a fluid flow. More specifically, the invention is the use of ultrasonic measurements from scatterers within the fluid to obtain both local speed of sound and local fluid velocity.

As used herein, the term "scatterer" refers to any feature within the fluid that exhibits a change in the speed of sound through that feature. Most often a change in density defines the scatterer, for example a particle. A change in density may also be the result of fluid density variation resulting from a temperature gradient, concentration gradient or other gradient. Ultrasonic scatterer is a feature that scatters ultrasonic sound or energy and exhibits a change in the speed of ultrasonic sound.

BACKGROUND OF THE INVENTION

Rheology describes the relation between the strain or rate of strain field and the stress field. In simple flows, viscosity is a single parameter that links the rate of shear and the shear stress in the flow field. However, in most real, industrial fluids, where the fluids are multi-phase and complex (solid-liquid dispersions and suspensions), the viscosity cannot be represented in terms of a single parameter and becomes a function of the flow field. It is well known that in a solid-liquid slurry, the local fluid viscosity not only depends on the local concentration of the solids but also on the local rate of shear and its gradient. Often, the solids being transported in the pipeline migrate away from the solid walls and into the core of the flow. As a result, measurement of rheology of the fluid near the wall will yield erroneous results relative to the total flow cross section.

Rheological characterization of solid-liquid dispersions is commonly performed using off-line measurement devices. This approach has the disadvantage that once a sample is withdrawn from the process stream its rheological properties will begin to change. Most often, the fluids to be characterized have rheologies that intimately depend on the flow field. This dependence is especially true for colloidal suspensions in which size and fractal dimensions of the clusters or aggregates depend strongly on the environment under which they exist. Many of these fluids exhibit shear-dependent viscosity, in the form of shear thinning or shear-thickening behavior, requiring determination of their viscosity at various shear-rates which correspond to the range of shear rates observed in the flow field. Off-line measurements can hardly reproduce the same conditions which exist in a real flow field such as shear induced migration of solid particles. Further, given that the material in the pipeline may not be homogeneous, it will be difficult to obtain a representative sample for off-line measurements.

Existing real-time on-line process monitoring rheometers monitor the properties of a side stream of material (Dealy, J. M. And Wissbrun, K. F., 1990, "Melt Rheology and Its Role in Plastics Processing," Van Nostrand Reinhold, New York). The steady shear viscosity is measured at a single shear rate (or flow rate). To obtain viscosity at various shear rates, either the flow rate in the side stream is controlled by an auxiliary pump or several parallel or serial side streams at different flow velocities are produced. For example, the current capillary viscometry technology uses an auxiliary pumping capacity and by cascading a series of capillary tubes, which limits the number of data points to the number of tubes, provides multiple-point viscosity measurements.

Commonly used for measurement of liquid carrier flow rates, ultrasonic Doppler flowmeters can yield the mean velocity inside of a pipe or in a flow field (Fowlis, W. W., 1973, "Liquid Metal Flow Measurements Using an Ultrasonic Doppler Velocimeter," *Nature Phys. Sci.*, 242, pp. 12–13). This approach relies on the principle that the frequency of a longitudinal acoustic wave, reflected from discontinuities or scatterers moving with the flow stream, is shifted. FIG. 1 depicts the most common orientation of the transmitter 100 and receiver 102 probes with respect to a pipe 104 and a fluid 106 flowing therein. The difference between the transmitted and received frequencies (frequency shift) is directly proportional to the discontinuity or scatterer velocity.

$$\frac{\omega_R - \omega_T}{\omega_T} = \frac{2v\cos\theta}{c} \quad (1)$$

where v is the convection velocity, c is the speed of sound, and θ is the half angle between the transmitted and received beams of ultrasonic energy. By assuming that the scatterers move at the same velocity as the fluid, one obtains the flow velocity. Numerous papers have been written on this topic, dating back to the U.S. patent to Chilowski, C. and Langevin, P., 1923, "Production of Submarine Signals and the Location of Submarine Objects," U.S. Pat. No. 1,471, 547. Today, this device could yield accuracies on the order of 1% of full scale. An estimated ten thousand or more of ultrasonic Doppler flowmeters are currently being used in the process industries such as pulp and paper, minerals, and power industries. Comprehensive reviews of the commercially available ultrasonic Doppler flowmeters are provided in Lynnworth, L. C., 1989, "Ultrasonic Measurements for Process Control—Theory, Techniques, Applications," *Academic Press*, San Diego, Calif. Lynnworth (1989), and Asher, R. C., 1983, "Ultrasonic Sensors in the Chemical and Process Industries," *J. Phys. E. Sci. Instrum.*, 16, pp. 959–63.

Reflection-mode and transmission-mode ultrasonic tomographic imaging systems have been well developed during the past few decades. A thorough review of these systems is provided by Plaskowski, A., Beck, M. S., Thorn, R., and Dyalowski, T., 1995, "Imaging Industrial Flows," *IOP Publishing, Ltd*, Bristol. The use of transmission-mode ultrasonic tomography for measuring the three dimensional velocity profile in a pipe has been demonstrated by Johnson, S. A., Greenleaf, J. F., Hansen, C. R., Tanaka, W. F., Lent, A., Christensen, D. A., and Woolley, R. L., 1977, "Reconstructing Three-Dimensional Fluid Velocity Vector Fields from Acoustic Transmission Measurements," *Acoustical Holography*, 7, L. W. Kessler Ed., Plenum Press, New York, and Hildebrand, B. P. and Liem, R., 1985, "Ultrasonic Tomography for Measuring Mass Flow Rates and for Mapping Spatial Distribution of Fluid Flows," Final Report for DOE Contract DE-AC03-84ER80150. Most of the systems are based on a transmission-mode fan beam projection in which the signal transmitted by a transducer is received by several transducers on the opposite side of the pipe. Due to the serious refractive effects associated with acoustic transmission through a metal pipe at off-normal views (off diametrical axis), parallel projections, such as those obtained with x-ray and γ-rays, have been shown to be impractical for true non-intrusive ultrasonic techniques (i.e., transducers located outside the pipe wall as in the case of clamp-on devices.). However, drill-thru flush-mounted transducer installations have been shown to produce fairly robust signatures in metal pipes with very little effect on the flow field as reported by Lynnworth, L. C., 1989, "Ultrasonic Measurements for Process Control—Theory, Techniques, Applications," *Academic Press*, San Diego, Calif.

In a tomographic imaging system, the object space is viewed from several parallel projections. These projections are essentially a series of time delay measurements in an acoustic system, giving the distances between the object-media interfaces from the receiving transducers. In the reflection-mode (pulse-echo), each transducer is used to transmit a short pulse and then receive the resulting reflected acoustic energy as a function of time. Unlike electrical resistive or capacitive impedance sensing technique, acoustic reconstruction algorithms are linear and straightforward. The output of the reconstruction process provides the echo strength versus time delay. The strength of the echo is a function of the sector angle aperture, local gradient of concentration of the slurry (gradient of acoustic impedance), and opacity of the mixture along the pathlength of the beam if the mixture is attenuative. The time delay axis may be converted to a distance (range) from the knowledge of local acoustic velocity.

$$X(t) = \int_0^t c(t\prime) dt\prime \quad (2)$$

where c is the local acoustic velocity or local speed of sound and X is the range. It has been assumed that the local speed of sound is a constant over the entire measurement range, thereby the range is directly proportional to the range time delay. The average speed of sound is found from two opposite transducers placed across the pipe. Thus, the variance in measurement of the range directly depends on the variance in the local speed of sound or concentration of the medium. If the local concentration of the slurry changes dramatically from one point to the next in the flow field, then the range will have a substantial amount of variance and the resulting measurement will be inaccurate. Although data exists for monodisperse particle slurries which show the dependence of the speed of sound on the slurry concentration (Kytömaa, H. K., 1995, "Theory of Sound Propagation in Suspensions: A Guide to Particle Size and Concentration Characterization," *Powder Technology*, 82, pp. 115–121), the actual dependence of speed of sound on concentration would have to be determined for the particular slurry in question using off-line calibration.

In the transmission-mode (time-of-flight) tomography, an ultrasonic wave is transmitted by one transducer and received on the opposite side by a receiving transducer. In the case of an invariant velocity field, the time-of-flight from the transmitter to receiver is $$\tau_{TR} = \int_T^R \frac{ds}{c}. \quad (3)$$

For a discretized field, the above equation turns into I rays and along each ray m cells. Thus a system of I linear equations are obtained. If the number of independent measurements through each cell becomes sufficiently large (>m), then the equations may be solved for the unknown component c in each cell. Addition of a fluid velocity vector usually complicates the matter since the velocity of sound in each cell becomes directionally dependent.

$$\tau_{TR} = \int_T^R \frac{ds}{c + s \cdot v} \quad (4)$$

where v is the convection velocity and s is the unit vector along the ray path. The scalar and vector effects may be separated out by calculating the sum and difference of measurements of time-of-flight taken from the same path. The resolution in the time-of-flight measurement is limited to the points at which different rays cross. As the number of projections (rays from different directions) increase, the resolution in velocity measurement improves.

In summary, the reflection mode or the pulse-echo technique is considered more suitable for the measurement of the convection of fluid velocity. However, speed of sound measurements may be more simply obtained using the transmission mode or the time-of-flight measurements, but at a lower spatial resolution.

Brunn, P. O., Vorewerk, J., and Steger, R., 1993, "Optical and acoustic rheometers: three examples," *Rheology* 93, March 1993, pp. 20–27; and Vorwek, J., Steger, R., Teufel, M., and Brunn, P. O., 1994, "Use of an optical meter to measure the flow rate and apparent viscosity of non-Newtonian fluids," *Flow Meas. Instrum.*, Vol. 5, No. 1, pp. 51–57 discuss ultrasonic measurements of the local shear rate as determined from the measured local velocity in the pipe. This was achieved by using an ultrasonic reflection-mode (pulse-echo) Doppler velocity mapping system. The principle of operation of the system is as follows: Ultrasonic transmission time-of-flight measurements can be used to determine the integrated line-of-sight acoustic velocity in the fluid. If the fluid contains scatterers (e.g. particles), then a coherent reflection system can be used to measure the Doppler frequency shift caused by the fluid flow. The magnitude of the Doppler shift can be used to determine the fluid velocity. Applying a sequence of range gates to the Doppler measurements allows determination of the fluid velocity profile along the line-of-sight of the ultrasonic transducer. When the acoustic velocity is uniform across the cross-section of the pipe, and is axisymmetric then this range-gated ultrasonic Doppler data can provide accurate measurement of the fluid velocity profile.

In pipes involving flow of complex fluids of unknown or varying properties, both the fluid velocity profile and the acoustic velocity are non-uniform across the cross-section of the pipe. The time-of-flight acoustic transmission measurement will be in error because the fluid velocity profile is not taken into account, and the reflection Doppler measurement will be in error because the acoustic velocity profile is not known. This will cause a distortion of the fluid velocity profile measured by the ultrasonic Doppler system, because the Doppler shift is proportional to the acoustic velocity and the range gate mapping assumes a uniform acoustic velocity across the pipe. Thus, a single line measurement cannot accurately solve the complex pipe flow velocity problem. The transmission measurement can only solve for the average acoustic velocity, not the acoustic velocity profile. The reflection Doppler measurement requires the acoustic velocity profile in order to determine the actual fluid velocity profile. A single line-of-sight measurement system does not provide enough information to simultaneously solve for both the acoustic and the fluid velocity profiles.

Accordingly, there is a need in the field of acoustic fluid velocity measurement for a method and apparatus that provides an accurate acoustic and fluid velocity profiles with high spatial resolution for fluids having spatially varying speed of sound.

SUMMARY OF THE INVENTION

According to the present invention, a method and apparatus rely upon tomographic measurement of the speed of sound and fluid velocity in a pipe. The invention provides a more accurate profile of velocity within flow fields where the speed of sound varies within the cross-section of the pipe. This profile is obtained by reconstruction of the velocity profile from the local speed of sound measurement simultaneously with the flow velocity.

The method of the present invention is real-time tomographic ultrasonic Doppler velocimetry utilizing a plurality of ultrasonic transmission and reflection measurements along two orthogonal sets of parallel acoustic lines-of-sight as depicted in FIGS. 2a, 2b, and 2c. The fluid velocity profile and the acoustic velocity profile are determined by iteration between the following two steps until convergence is reached. This iteration will improve accuracy but in general is not required for velocities much smaller than speed of sound.

(1) Reflection-mode pulsed wideband Doppler measurement determines the approximate fluid velocity profile along each line-of-sight assuming that the acoustic velocity is known (initially constant).

(2) Transmission measurements of time-of-flight between opposing transducers provide measurement of the integrated line-of-sight acoustic velocity at a plurality of positions across the pipe cross-section. Utilizing tomographic inversion, the acoustic velocity at each intersection point is determined assuming that the fluid velocity is known (initially assumed known).

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
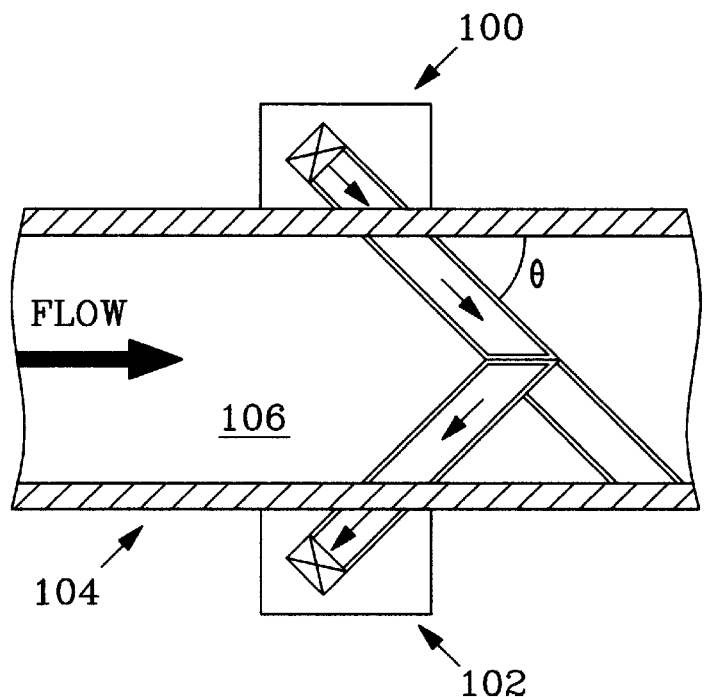
FIG. 1 shows a prior art transducer pair for an ultrasonic flowmeter.
Figure 2A:
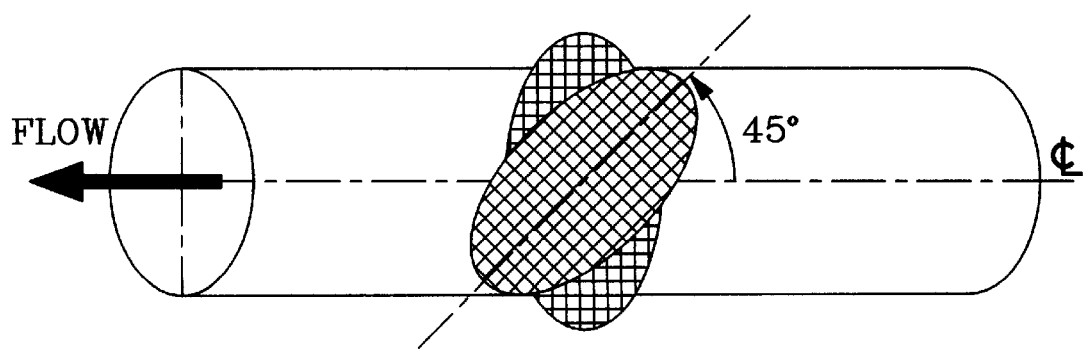
FIG. 2a shows orthogonal lines of sight through a fluid volume.
Figure 2B:
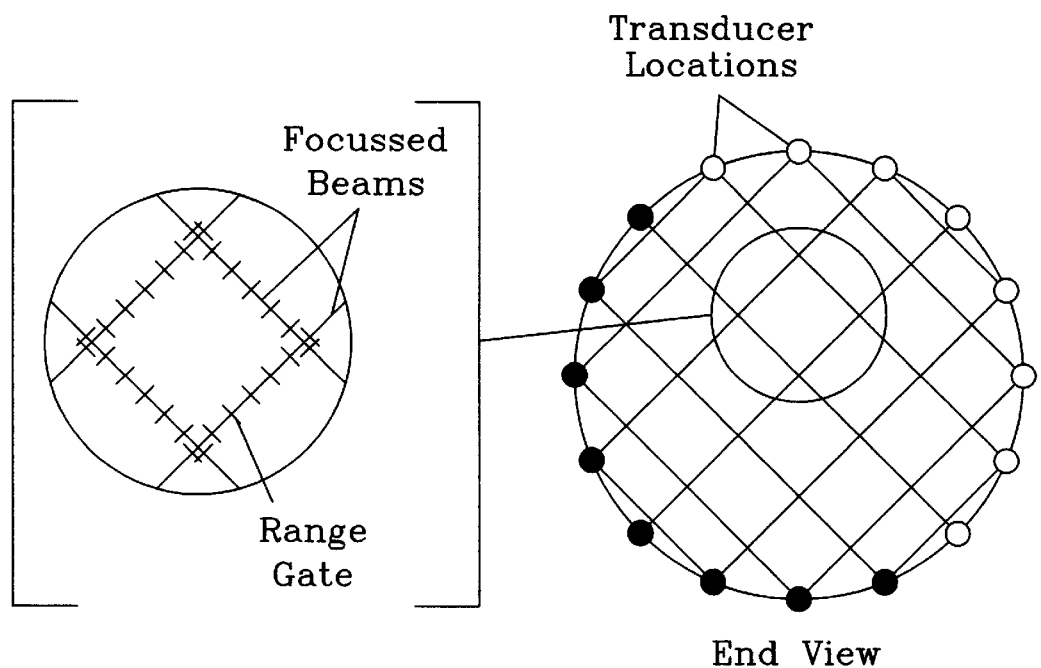
FIG. 2b shows a transducer grid.

For a polydisperse slurry, or a slurry of colloidal aggregates, where the wave-particle interaction may be in any of the different regimes, it becomes a formidable task to separate out the relation between attenuation and concentration from all the remaining effects. The local attenuation can be measured tomographically from the transmitted energy using the transducer grid shown in FIG. 2b or 2c. Alternatively, the relation between speed of sound and concentration is more direct and achievable for concentration measurement in a slurry. The local speed of sound is measured via time-of-flight measurements. The relation between the concentration and speed of sound is established through a one-time off-line calibration for each slurry being transported. This correlation is then used to infer the local concentration in the pipe.

The method of the present invention for local fluid velocity measurement relies on measurement of the Doppler frequency shift of moving tracer particles, or scatterers, within a pipe flow. Using a short ultrasonic pulse system, the cross-sectional velocity profile is obtained from the Doppler shift at each point in range.

The Doppler frequency shift is given by $$f_D = \frac{2v}{c}f$$

where v is the particle velocity, c is the speed of sound in the fluid, and f is the ultrasonic frequency. For example, the Doppler shift for a particle moving with velocity of 1 m/sec in water with speed of sound equal to 1500 m/sec, and an ultrasonic frequency of 5 MHz is 6.67 kHz.

In order to obtain good range resolution it is essential to transmit a short ultrasonic pulse. The range resolution is approximately equal to one-half of the spatial width of the pulse. For N sine-wave cycles of wavelength $\lambda$, the range resolution is approximately $$\Delta_R = N\frac{\lambda}{2}.$$

For example, 5 cycles of 5 MHz (0.3 mm wavelength) yields a range resolution of approximately 0.75 mm. Obtaining such high range resolution creates a problem for measurement of the Doppler shift which is on the order of kiloHertz. A gated sine-wave of only a few cycles has a relatively wide frequency bandwidth B of approximately, $$B = \frac{f}{N}$$

which is 1 MHz for 5 cycles of a 5 MHz wave. The Doppler shift would need to be on the order of or larger than 1 MHz to be distinctly measurable from the frequency spectrum of the echo returned from the particles. Doppler shifts this large would only be expected if the fluid velocity were on the same order as the speed of sound in the fluid. Velocities of interest in pipe flow problems are much lower than the speed of sound. While reducing the bandwidth would allow for good Doppler velocity resolution it would yield a poor range-resolution. This conflict is resolved according to the present invention by transmitting and receiving multiple pulses, i.e. observing the fluid over a much longer time interval and obtaining a greater number of observations from each point in the flow field. Multiple pulses, or a plurality of pulses, is at least two pulses, preferably about 5 pulses with no limit of the number of pulses that may be used.

Figure 2C:
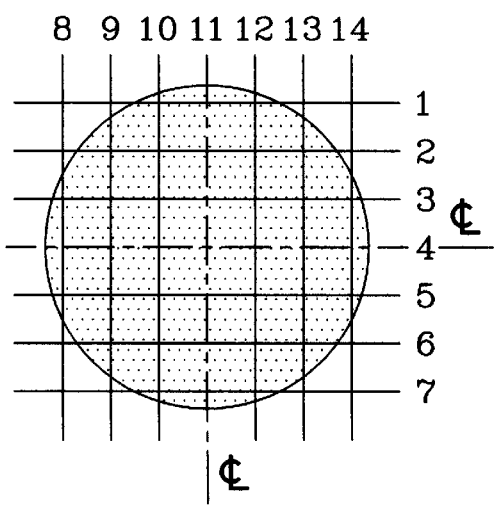
FIG. 2c shows an alternative transducer grid.
Figure 2D:
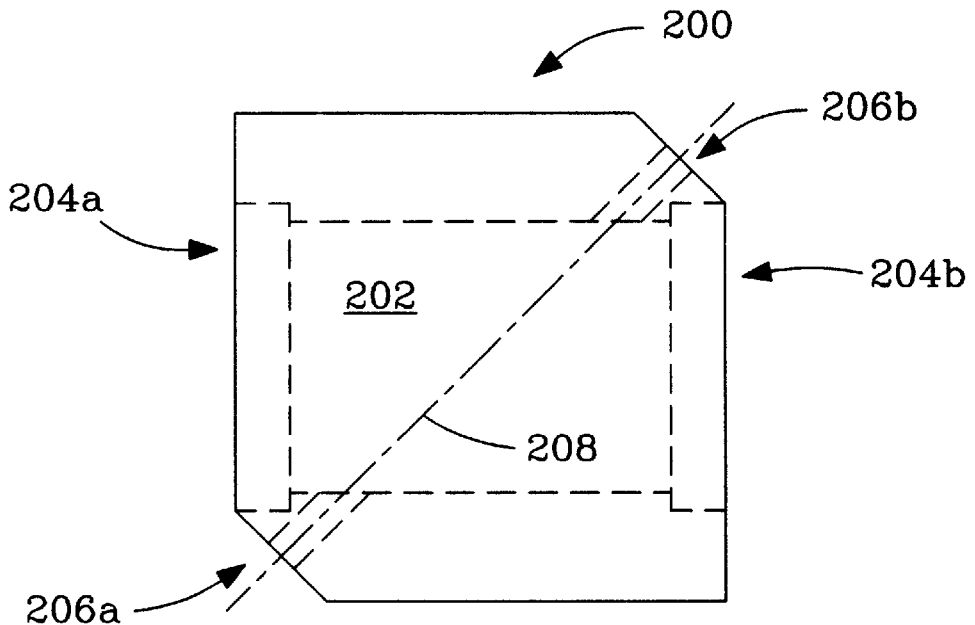
FIG. 2d is a side view of a transducer block.
Figure 2E:
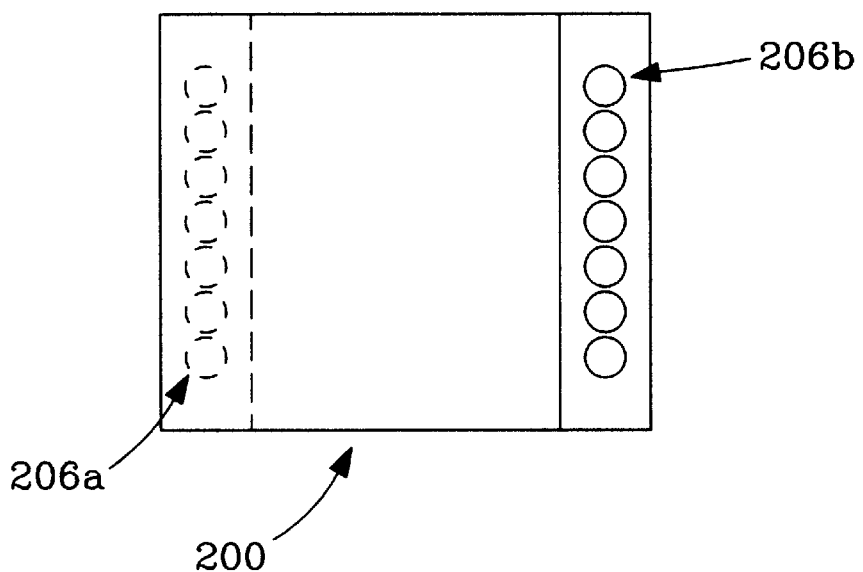
FIG. 2e is a top view of the transducer block.

The grid may be achieved in part with the transducer block shown in FIGS. 2d and 2e. The block 200 has a flow passage 202 and pipe connection ports 204a, 204b. Transducer ports 206a, 206b are aligned along a common axis 208.

Figure 3:
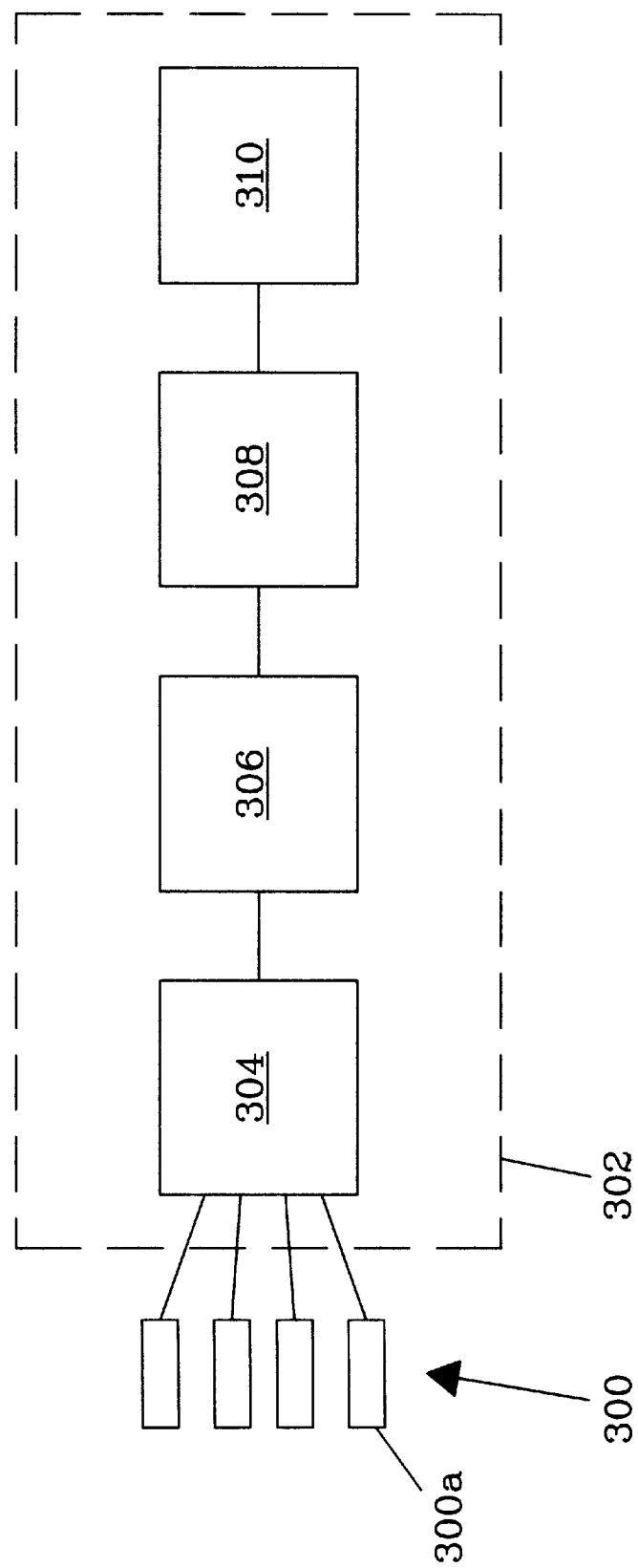
FIG. 3 is a block diagram of the apparatus of the present invention.

The apparatus of the present invention FIG. 3 includes pairs of ultrasonic transducers 300 (shown schematically) connected to an ultrasonic Doppler computer data collection system 302. This system 302 has an ultrasonic transceiver 304 (e.g. Model XIM 1055 Transducer, Xactex Corporation, Pasco, Wash.), computer interface 306, analog-to-digital converter 308, and computer system 310. The ultrasonic transceiver 304 generates a specified number of cycles (preferably 5) of ultrasound, then amplifies and transmits them through the ultrasonic transducer 300a. The same transducer 300a is used to receive the echoes from the fluid scatterers. The received echo signals are passed through a low noise amplifier chain (within the transceiver) with gain adjustable to 99 dB. After amplification the received signals are coherently down converted in frequency from 5 MHz to baseband (centered at DC). Frequency downconversion allows a much smaller amount of data to be recorded by the A/D converter 308 than would direct A/D sampling. Computer interface electronics 306 generate the sampling clock pulses used by the A/D converter 308. This number of pulses is adjustable, as is the time delay to the first sample. After A/D conversion the data is stored on the computer systems disk-drive (within the computer system 310). Preferred parameters used in this system are shown in Table 1.

TABLE 1

The Ultrasonic Doppler System Parameters.

Data collection parameters

| | |
|---|---|
| Frequency | 5 MHz |
| Number of cycles | 5 |
| Range resolution | 0.75 mm |
| Range samples | 512 |
| Slow-time samples | 1024 |
| Time per waveform | 0.5 msec |
| Total data collection time | 0.512 sec |

Figure 4:
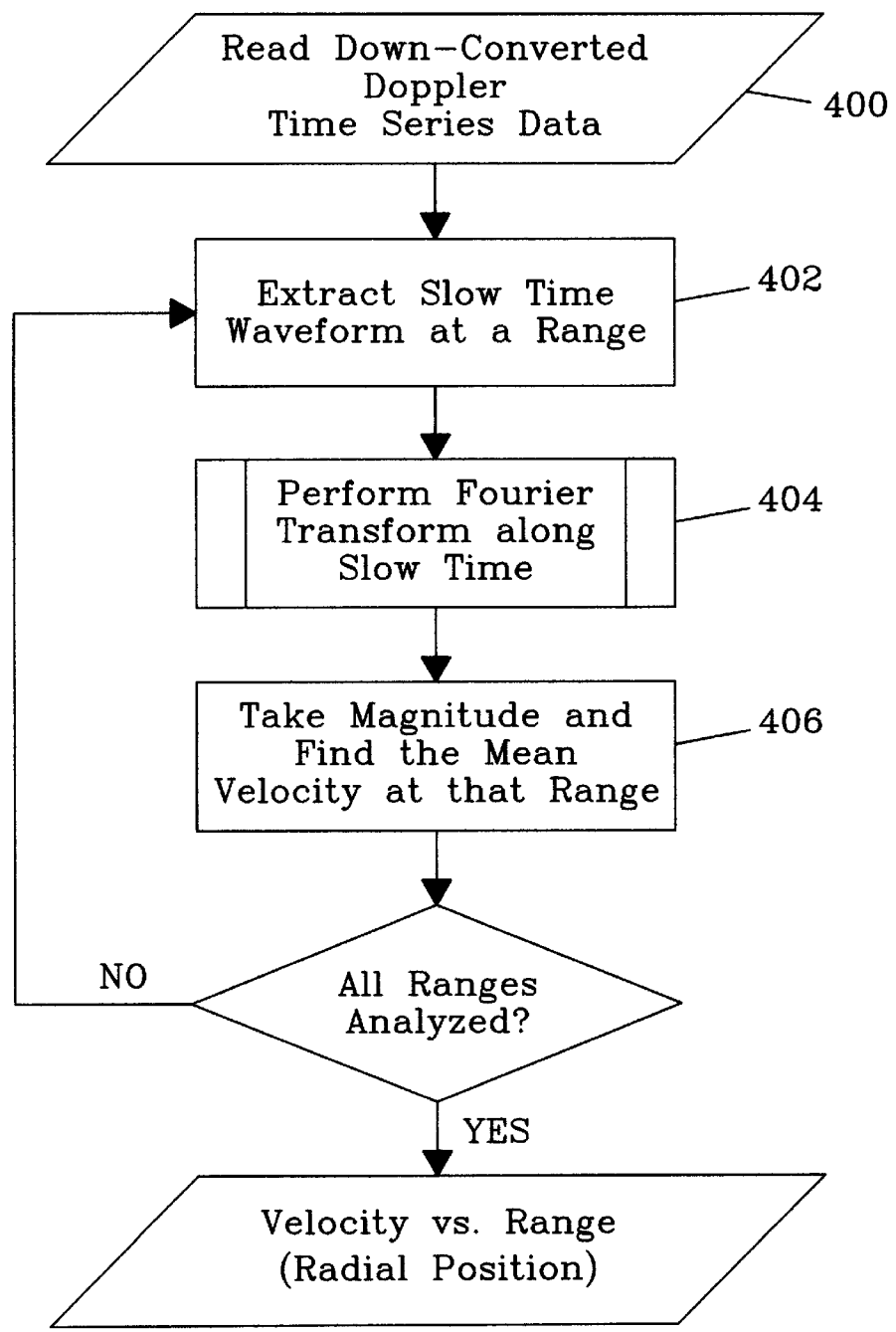
FIG. 4 is a flow chart of a first instruction set.

The first instruction set within the computer receives data from the Reflection-mode Doppler measurement and determines the approximate fluid velocity profile along each line-of-sight assuming that the acoustic velocity is known (initially constant). FIG. 4 is a flow chart of this first instruction set. The Doppler data is down-converted then read in a time series format by the computer 400. An initial range or "fast-time" is selected from which to extract a slow-time waveform 402. A Fourier transform is performed along the slow-time 404 from which is obtained the magnitude and the mean velocity at that initial range 406. The first instruction set is repeated until all ranges have been assigned a fluid velocity.

Figure 5:
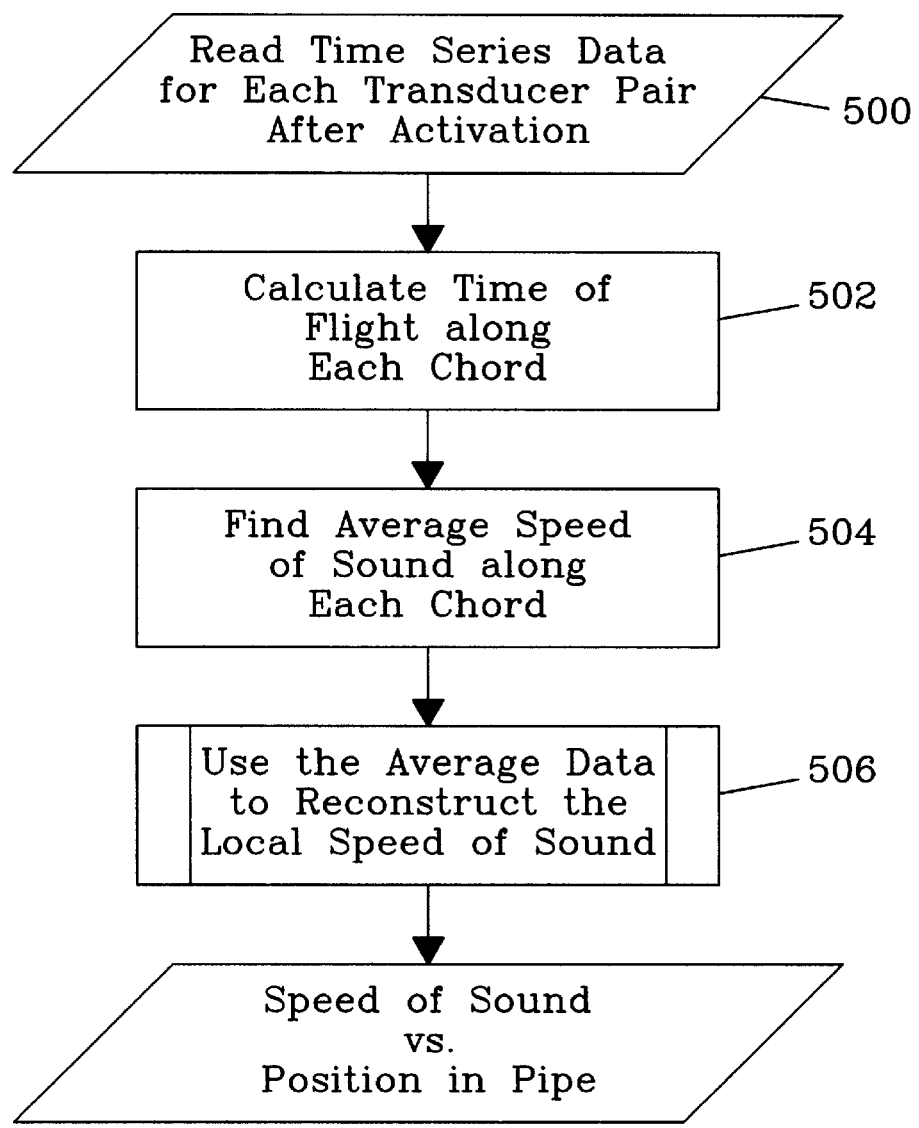
FIG. 5 is a flow chart of a second instruction set.

The second instruction set (FIG. 5) within the computer receives data from transmission measurements of time-of-flight between opposing transducers 500 and determines measurement of the integrated line-of-sight acoustic velocity at a plurality of positions across the pipe cross-section. The time-of-flight is calculated along each chord 502 and an average speed of sound is found 504. Utilizing tomographic inversion, the acoustic velocity at each intersection point is determined 506 assuming that the fluid velocity is known (initially assumed known).

According to the present invention, it makes no difference whether the first or second instruction set is done first, nor does it make a difference whether the Doppler or time-of-flight is measured first. The results from the first and second instruction sets are combined in Equation 2 but with the local speed of sound as a variable rather than a constant.

Experimental Apparatus

An experiment was conducted to measure a laminar velocity profile in a pipe for two different fluids, propylene glycol (a Newtonian fluid) and 0.1% by weight of aqueous Carbopol 980 solution (a yield pseudoplastic non-Newtonian fluid).

Figure 6:
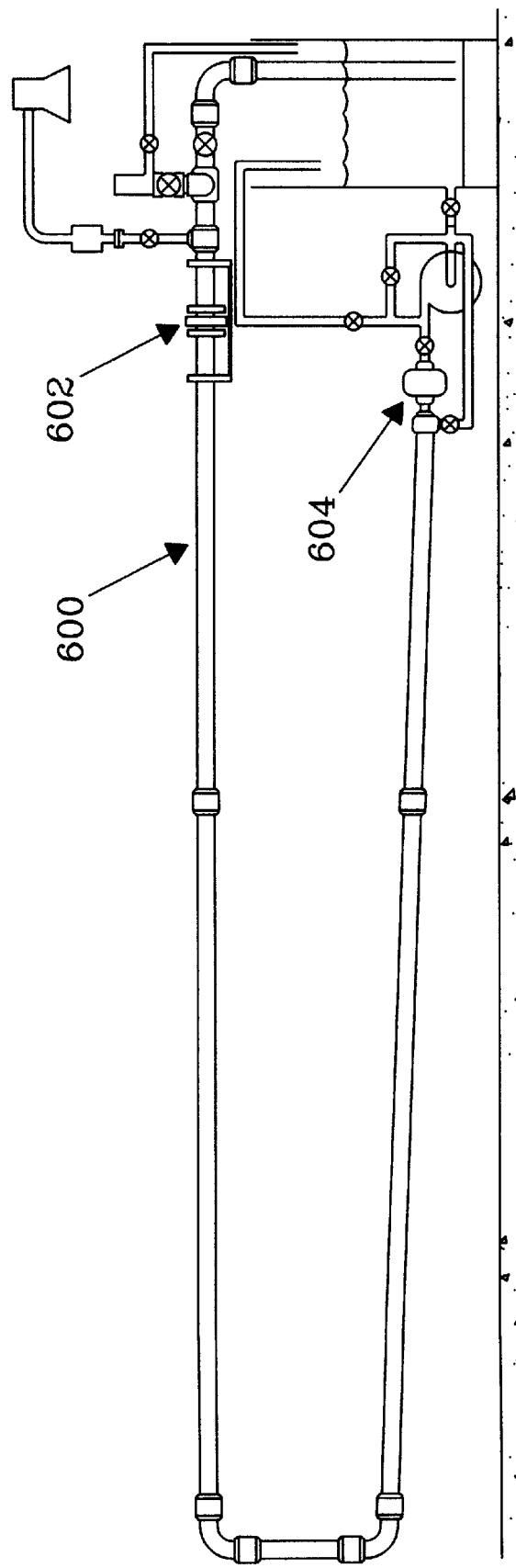
FIG. 6 is a side view of an experimental pipe loop.

A fully developed flow in a circular pipe was generated using the hydraulic system shown in FIG. 6. Flow was delivered to a 5.5 m long×5 cm diameter (nominal) straight PVC pipe section 600. The ultrasonic transducer block 602 was located far enough downstream such that the flow became fully developed with no swirl or secondary flow before reaching the transducers. The flow rate in the pipe 600 was measured using a positive displacement flowmeter 604. The flow rate in the system was laminar such that the Reynolds numbers for all the different conditions were smaller (to much smaller) than 300. For both Carbopol and propylene glycol solutions, sufficient back-scattering was present to produce a velocity profile. However, the signal-to-noise ratio was significantly improved by adding particles. Specifically, particles added were about 45 to 50 micron silver coated glass particles at approximately 0.5 vol%. Settling of particles was finite but not significant for the Newtonian case ($u_s/U<10^{-3}$), and almost non-existent for the non-Newtonian fluid which had a strongly shearthinning behavior.

Figure 7A:
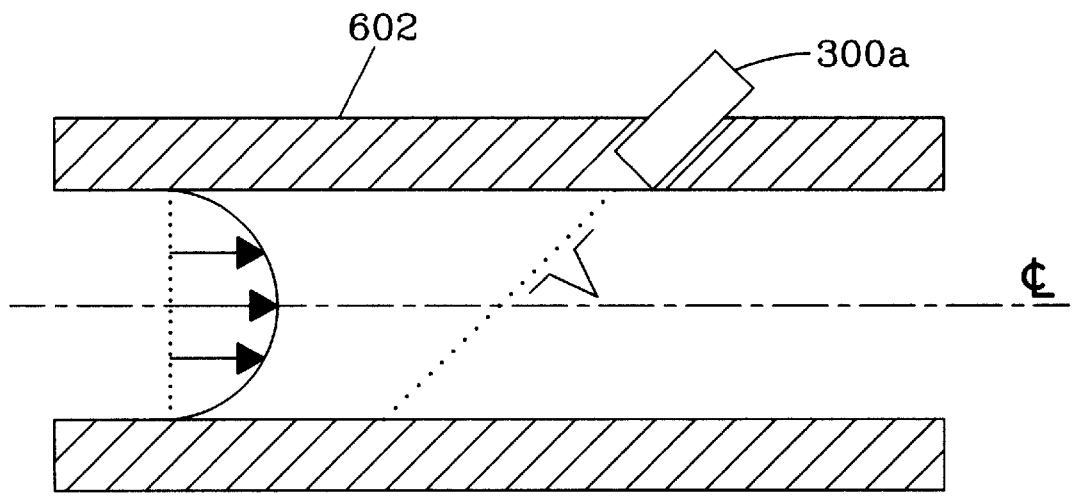
FIG. 7a is a single transducer block.
Figure 7B:
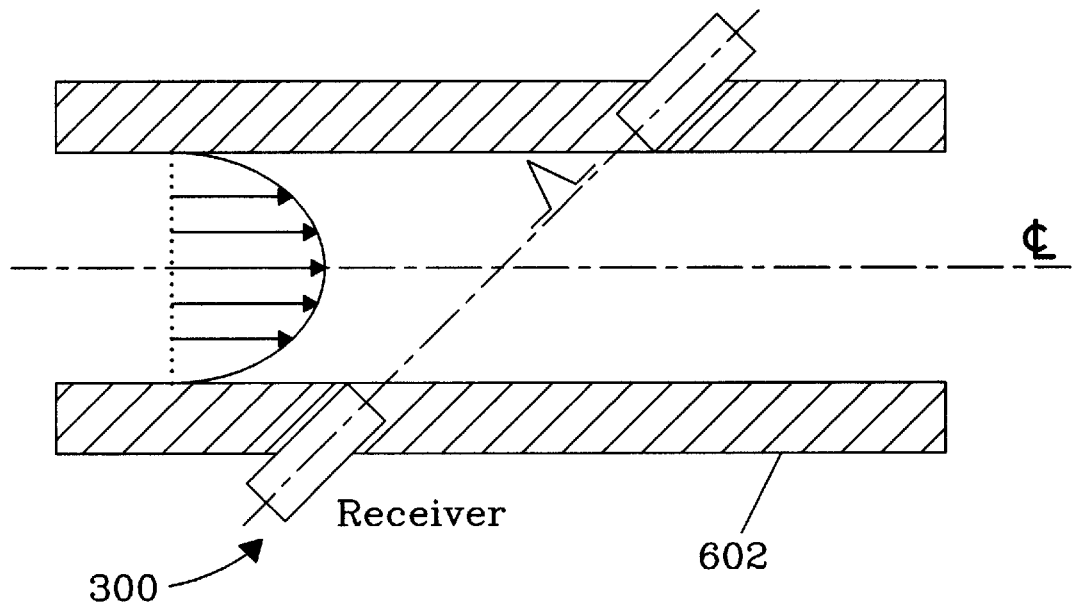
FIG. 7b is a paired transducer block.

FIG. 7a shows the transducer block 602 with a single transducer 300a. The axial velocity in the pipe was interrogated by this transducer 300a positioned at 45° with respect to the flow direction. FIG. 7b shows the orientation of a pair of opposing transducers 300 in the transducer block 602 installed on the pipe. For velocity profile measurements, the ultrasonic signal was transmitted into the pipe and return signal was received by the transceiver transducer and supplied to the data acquisition system 302 (FIG. 3). The processed signal was then converted into a velocity profile. For speed of sound measurements, the time-of-flight for the signal transmitted by the transceiver to reach the receiver was measured. To perform tomography, a grid of transducers (5 MHz) was placed around the pipe FIG. 2c. Two transducers 300 were placed along each chord—one for velocity measurement and the other for speed-of-sound measurement.

Figure 8:
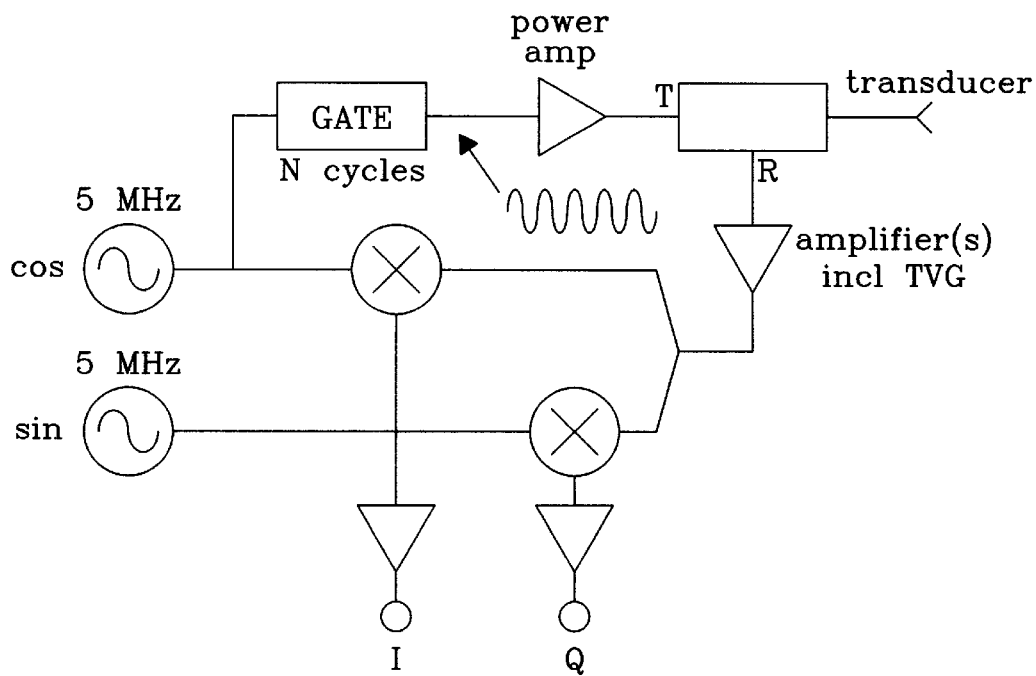
FIG. 8 is an electronic block diagram of the transceiver.

The waveform and number of cycles used for triggering the transceiver was generated using an electronic circuitry shown schematically in FIG. 8. Between 5 to 20 cycles were used depending on the particular experimental condition under study.

A dual-beam arrangement LDV (Laser Doppler Velocimeter) system (not shown) working on the backscatter mode was used to verify what the velocity distribution in the pipe is for both Newtonian and non-Newtonian fluids. The probe volume dimensions were approximately 0.1×1 mm. The two beams were aligned along the axis of the pipe such that the pipe curvature was not an issue for the axial velocity measurements.

EXAMPLE 1

An experiment was conducted to verify the present invention using a single transceiver in the transducer block (FIG. 7a).

Figure 9:
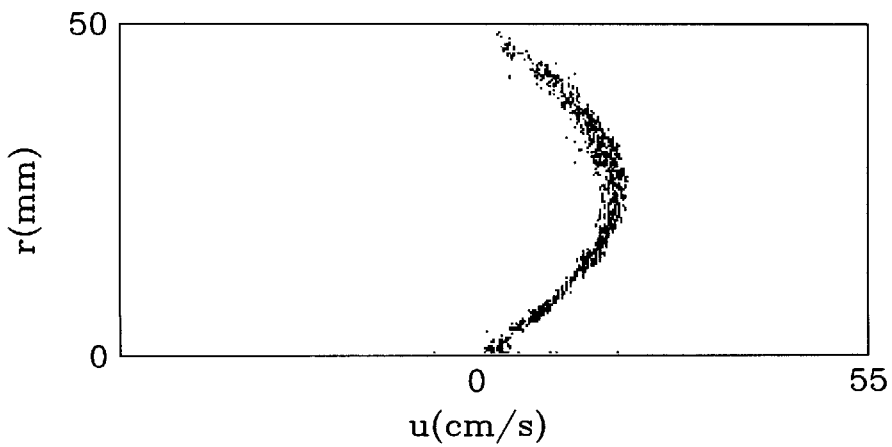
FIG. 9 is flow data from a single transducer.
Figure 10A:
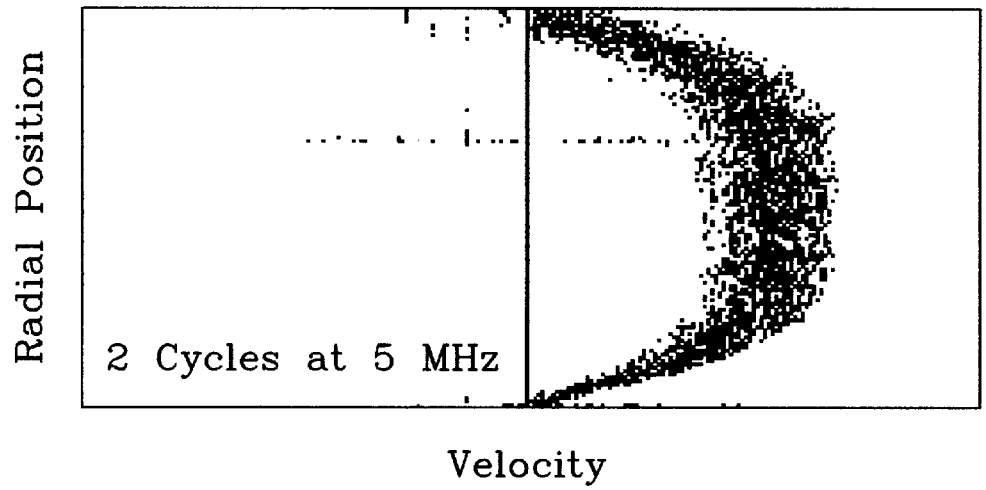
FIG. 10a is flow data using 2 cycles at 5 MHz.
Figure 10B:
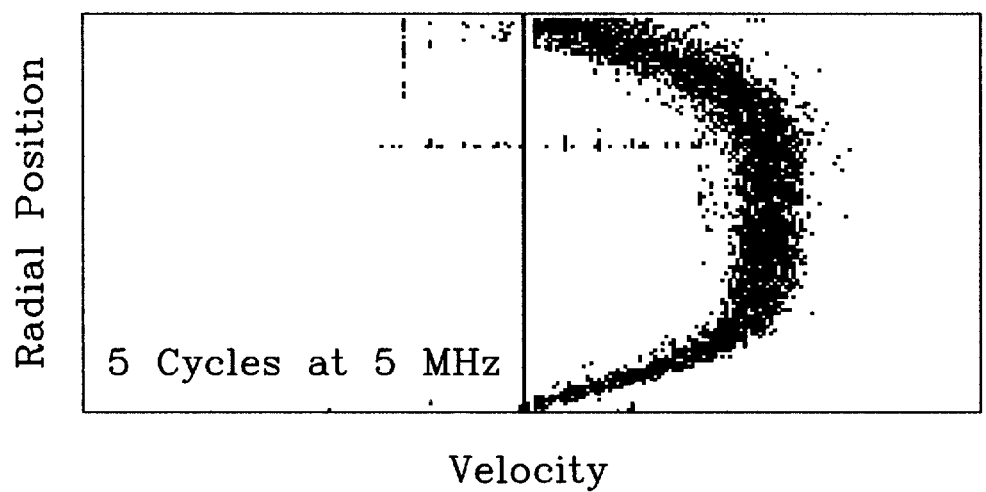
FIG. 10b is flow data using 5 cycles at 5 MHz.
Figure 10C:
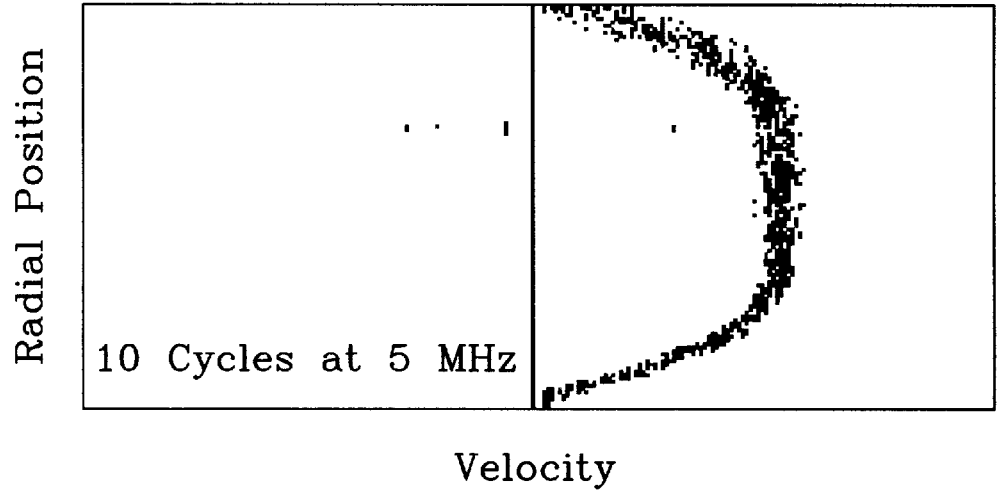
FIG. 10c is flow data using 10 cycles at 5 MHz.
Figure 10D:
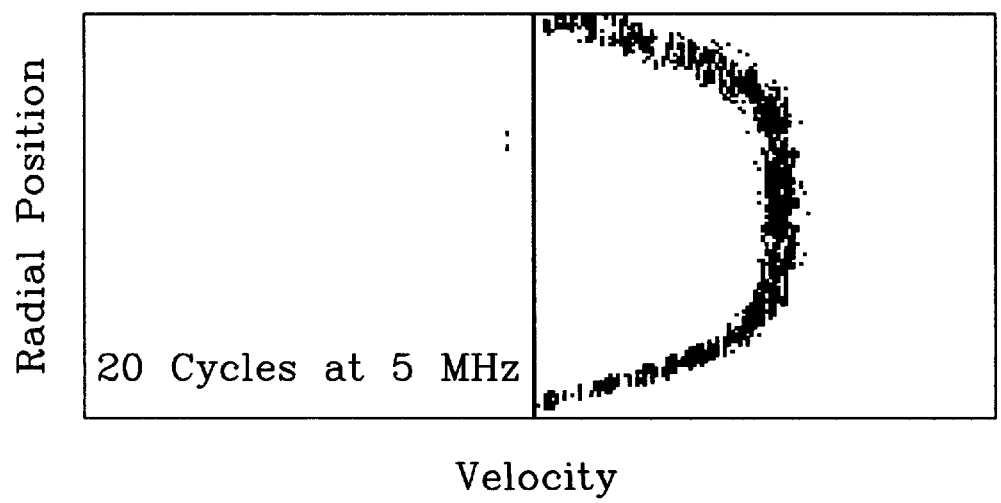
FIG. 10d is flow data using 20 cycles at 5 MHz.

Raw data from the pipe flow had a vertical axis of ultrasonic wave signal amplitude distribution representing the range, or fast-time axis which varied from 0 to 50 mm. The information along this axis is over-sampled by approximately five times since there are 512 sampled data points for approximately 100 range gates (defined as the path length divided by the range resolution). The horizontal axis, time, represents the slow-time axis which varies from 0 to 0.2 seconds. The frequency of this data along the slow-time direction (horizontal) is proportional to the local velocity and is the Doppler shift of the fluid. Since the Doppler shift is proportional to the fluid velocity, the velocity was obtained by Fourier Transform of the raw data. The signal period increases approaching the side-walls of the pipe (near 0 or 50 mm). The Fourier transform of the raw data is a velocity profile as shown in FIG. 9 specifically for flow of propylene glycol (Newtonian fluid) in the pipe measured with the UDV of the present invention. The distribution is parabolic with a centerline velocity being the same as the measurements made with LDV. The distribution of velocity shown on this plot is parabolic, as expected for a laminar Newtonian flow in a circular pipe.

Additional data are shown in FIGS. 10a, 10b, 10c, 10d. The speckled appearance of these profiles is due to the random nature of the incoming signal from the scatterers as well as finite domain FFT aliasing. Varying the number of cycles in a pulse transmitted into the fluid affected the velocity density function at each radial location by broadening as the number of cycles decrease from 10 to 2 cycles per pulse. However, increasing the number of cycles to 20 did not improve compared to the 10 cycle pulse conditions. Therefore, most of the experiments were performed with 5 or 10 cycle pulses.

Figure 11:
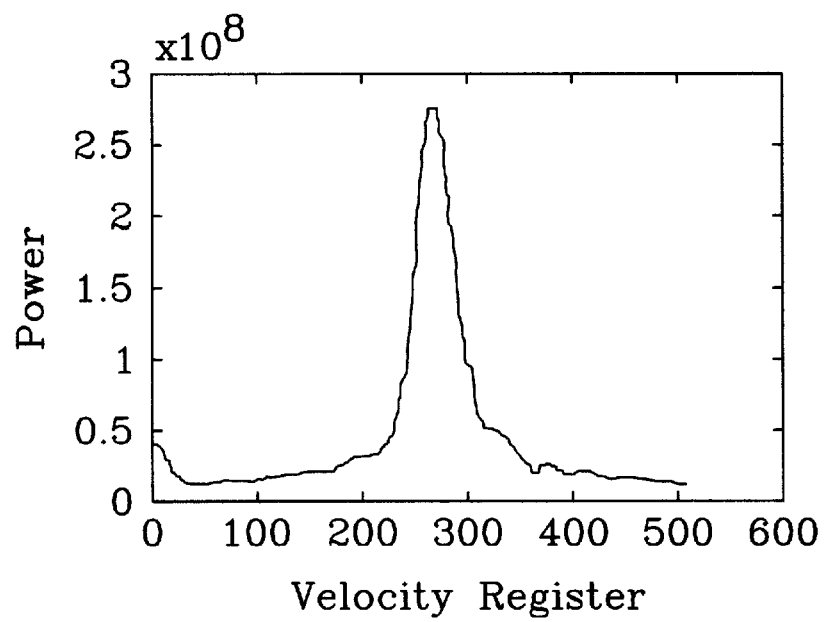
FIG. 11 is a probability density function for axial fluid velocity.

To obtain a unique velocity distribution from the images shown in FIGS. 10a, 10b, 10c, 10d, it was necessary to process the data further such that at each radial position a single number representative of the local velocity was obtained. The velocity at each radial location is represented by a probability density function (PDF). A typical PDF of velocity is shown in FIG. 11. This PDF was obtained by averaging over 0.512 sec which results in a rather smooth distribution. The peak of this distribution was selected as the maximum likelihood of the local velocity.

Figure 12:
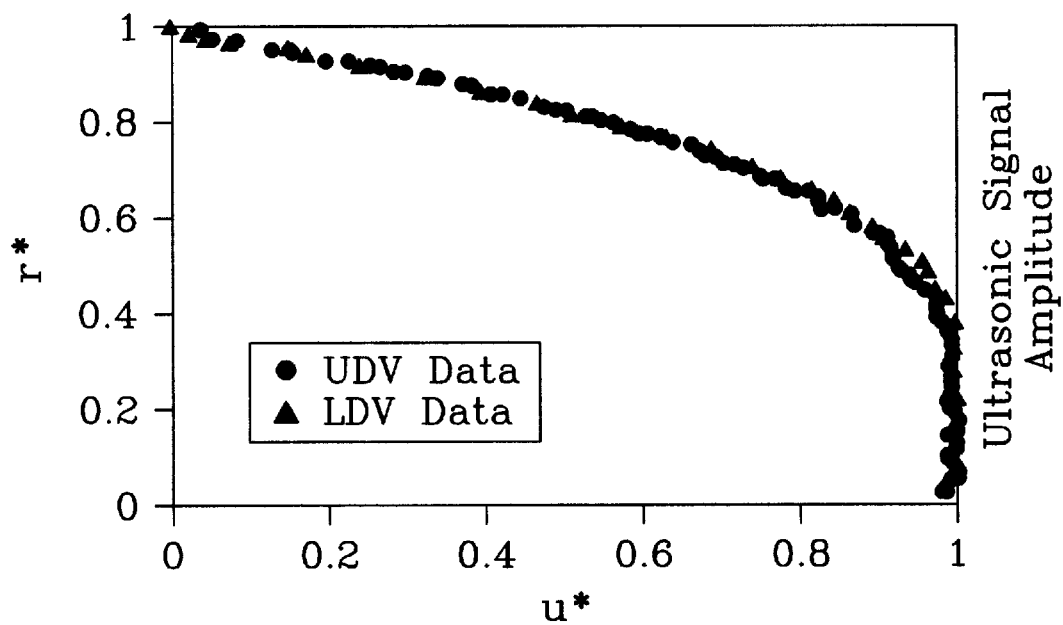
FIG. 12 is a fluid velocity profile comparing ultrasonic data with laser data.
Figure 13A:
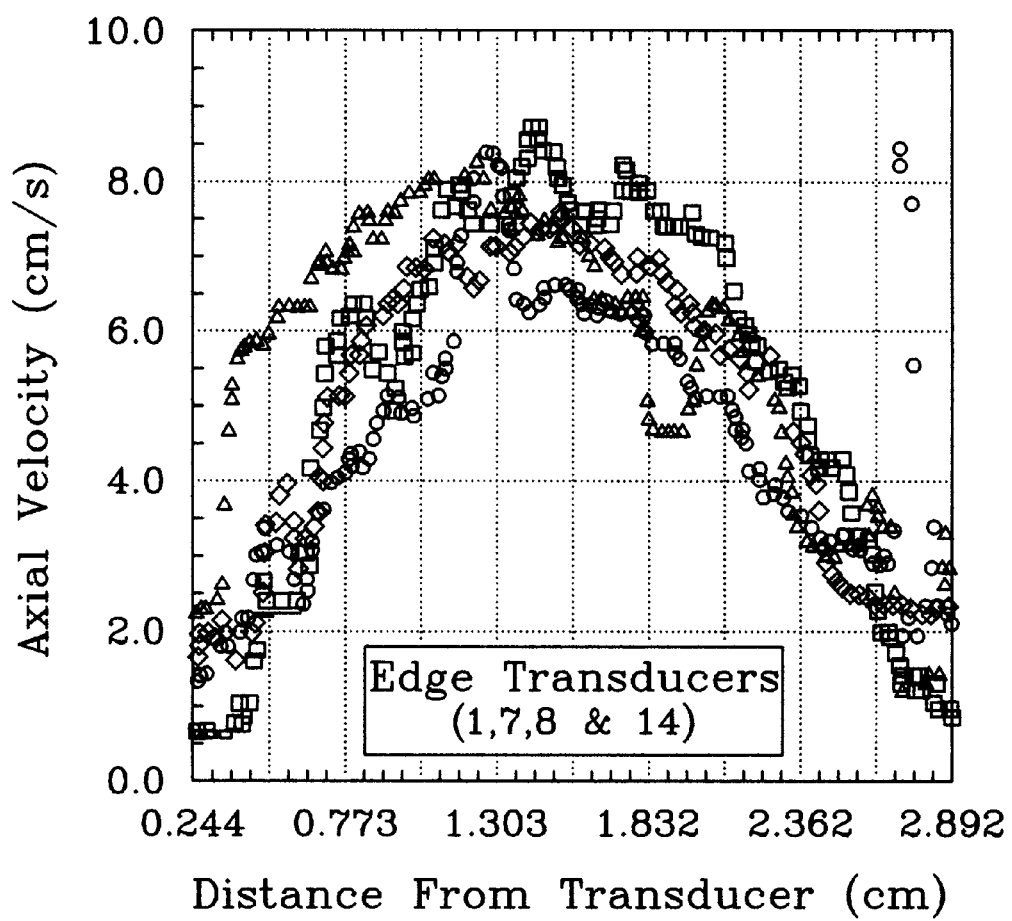
FIG. 13a shows velocity profiles from transducers pairs 1, 7, 8, & 14.
Figure 13B:
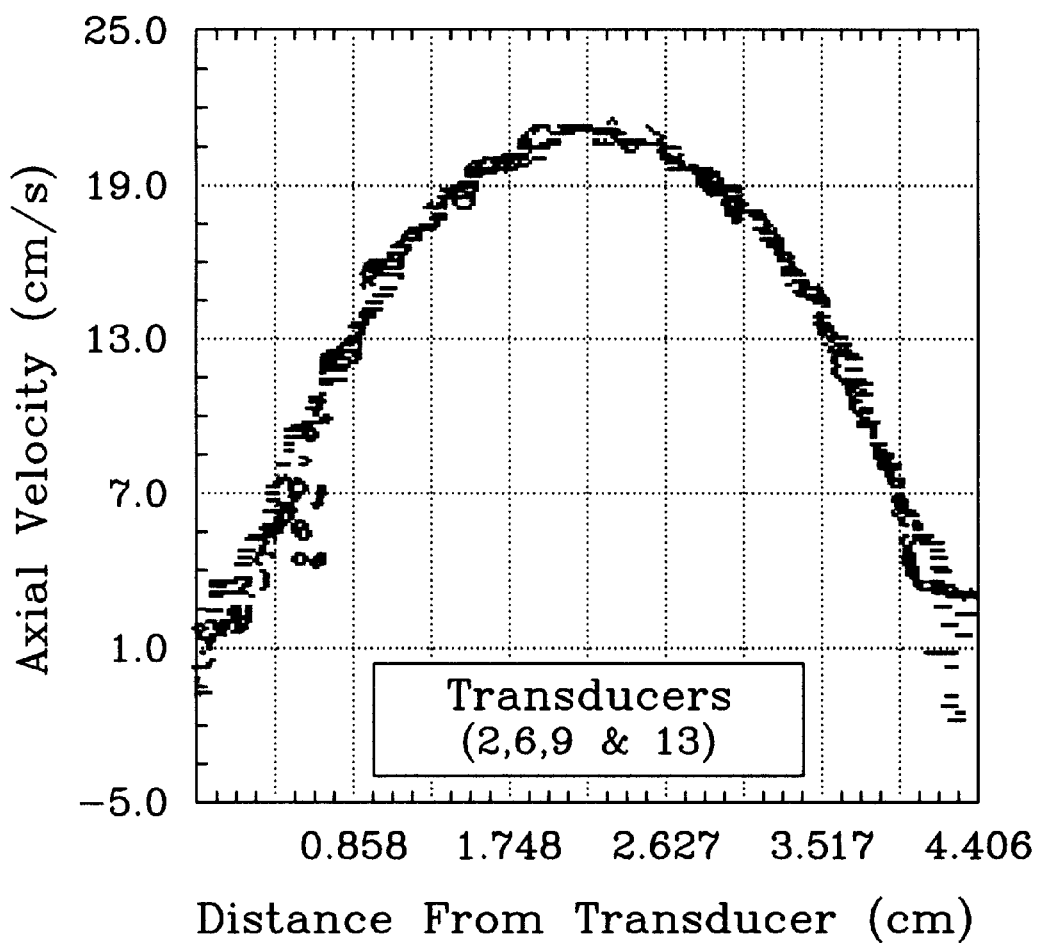
FIG. 13b shows velocity profiles from transducers pairs 2, 6, 9, & 13.
Figure 13C:
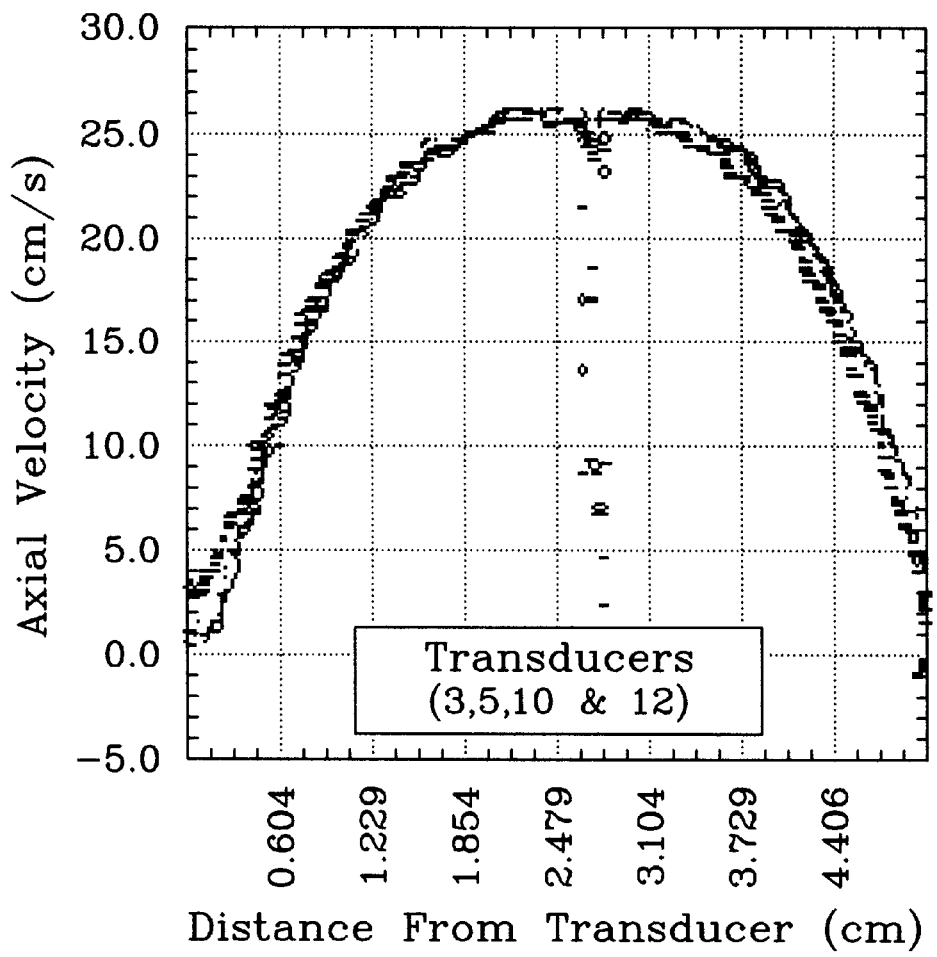
FIG. 13c shows velocity profiles from transducers pairs 3, 5, 10, & 12.
Figure 13D:
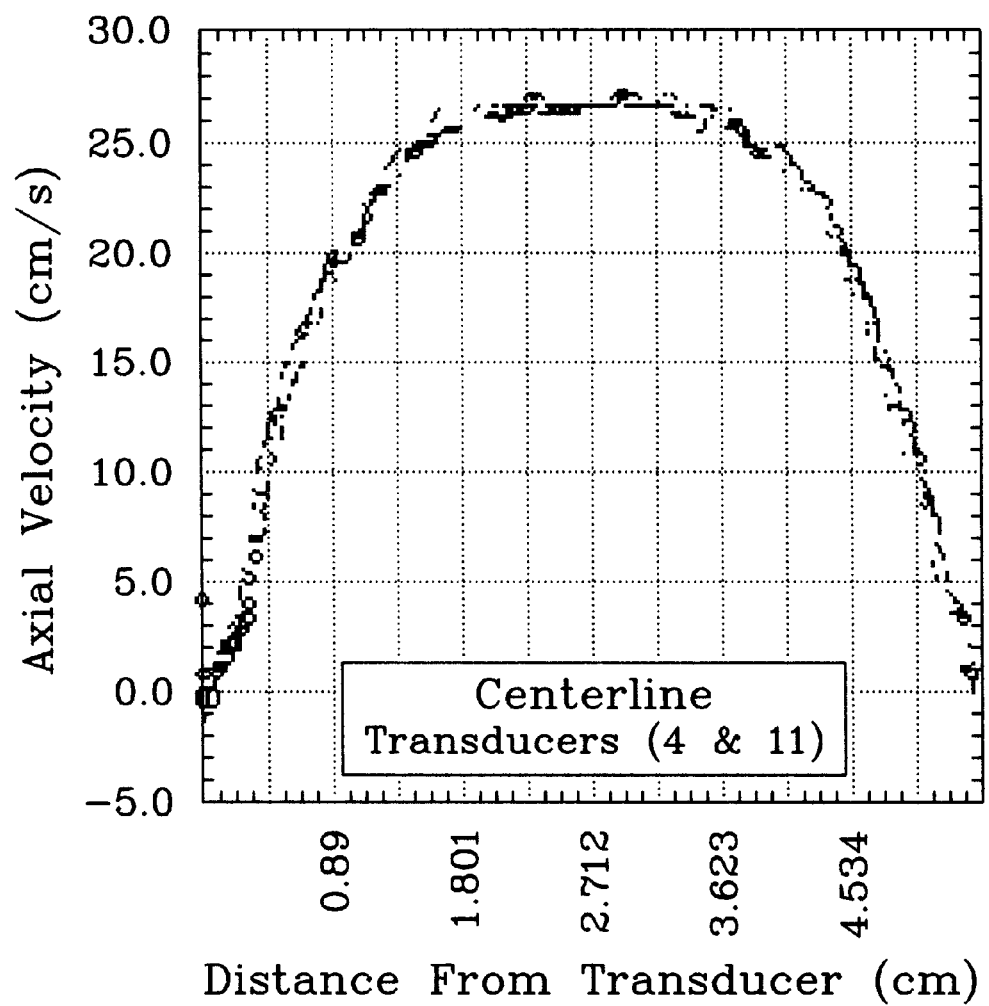
FIG. 13d shows velocity profiles from transducers pairs 4 & 11.

FIG. 12 shows the comparison between velocity profiles found with UDV and LDV for 0.1% by weight of Carbopol solution. Because of the presence of yield stress in the Carbopol solution, there tends to be a plug or unsheared region in the center of the pipe. This unsheared zone becomes larger and larger as the flow rate decreases and extends throughout the cross-section of the pipe as the flow rate diminishes. Note that the amplitude of velocity and the extent of the plug are measured very closely by both techniques. In most parts, the UDV and LDV measurements show less than 5% discrepancy. This is due to higher variance in UDV measurements at specific points in the pipe, caused by multiple reflection interference. That is the echo of the previous pulses created a high background noise level and as a result increased fluctuation in the measurements (see FIGS. 10a, 10b, 10c, 10d). Further, the UDV data seemed to show anomalous behavior near the wall caused by probe penetration into the wall. These two effects can be corrected by more careful design of the transducer block.

EXAMPLE 2

A further experiment was conducted using a plurality of transducer pairs to demonstrate the present invention.

The orthogonal grid arrangement shown in FIG. 2c was used for tomographic measurements of the velocity profile and speed of sound. For flows where settling or segregation of particles do not exist, or if the velocity profile is axisymmetric, the measurements along several of the chords shown should ideally be identical. Conversely, any flow nonuniformity due to lack of symmetry (coming from swirl or secondary flow in the pipe) or settling, saltation, or segregation in the solids within the pipe would be observable by comparison of the results obtained from the different symmetric chords. Of course in the current measurements for symmetric flow we did not expect to see any difference in the measurements made by symmetric transducers. Nonetheless, such measurement could provide an indication on the measurement uncertainty.

FIGS. 13a, 13b, 13c, and 13d show the velocity profile at different symmetric chords. Most of the velocity profiles at each chord closely overlap. The close agreement in the results is an indication of the reasonably low level of uncertainty in the measurements, indicating that not only the flow was very symmetric, but also the ultrasonic measurement approach produces repeatable and accurate results.

Figure 14A:
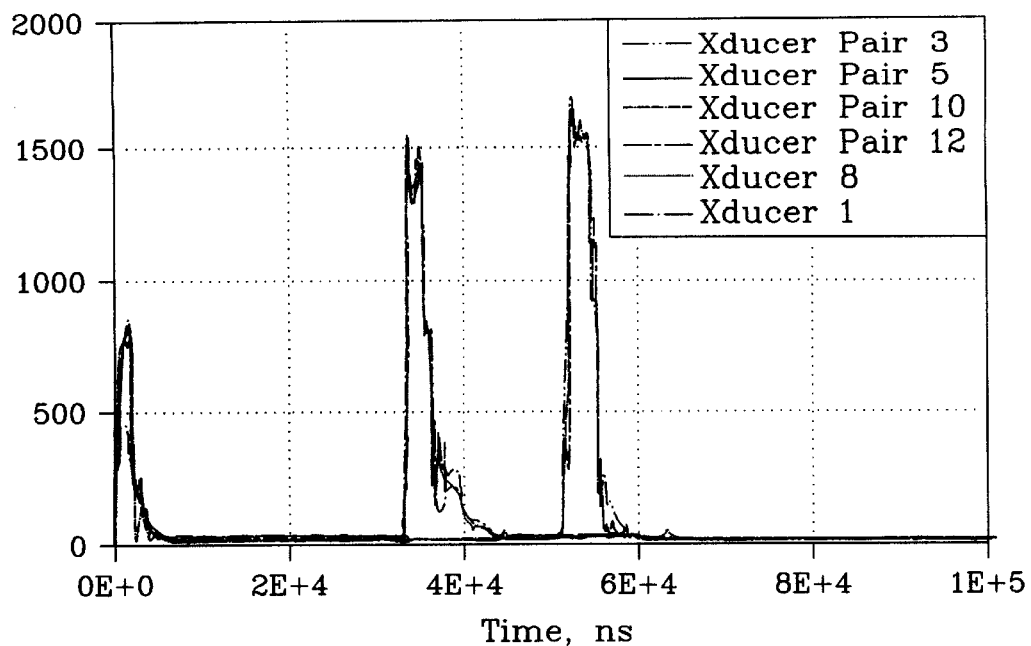
FIG. 14a is a comparison of transit time between transducer pairs 3, 5, 10, 12, 8, & 1.
Figure 14B:
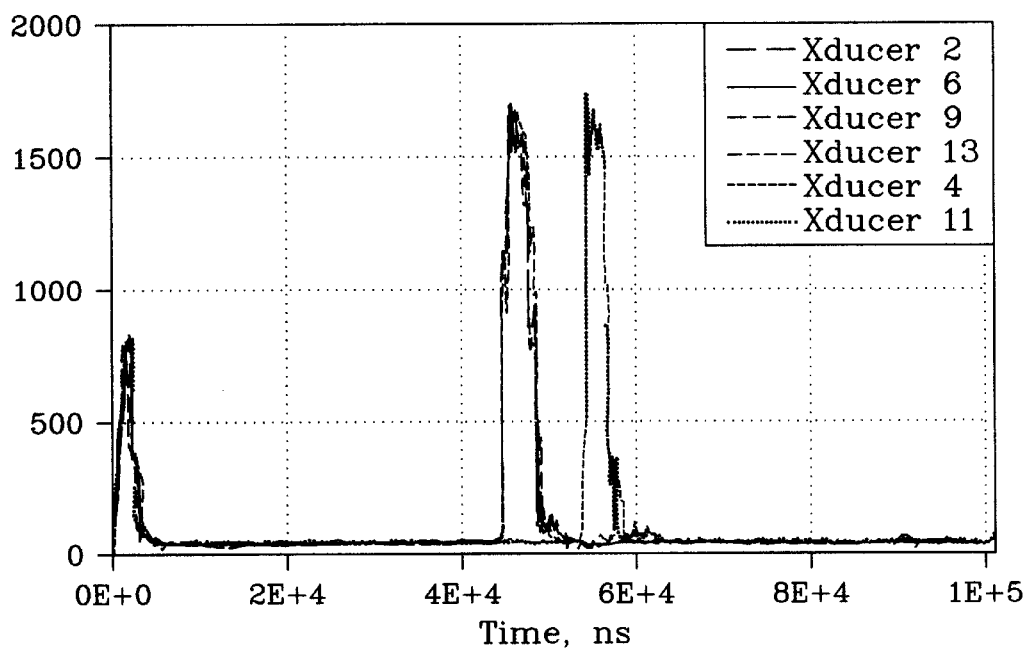
FIG. 14b is a comparison of transit time between transducer pairs 2, 6, 9, 13, 4 & 11.

FIGS. 14a and 14b are the time-of-flight measurements by various transducer pairs. Each figure includes the signal from two different groups of symmetric transducer pairs (e.g., 4 and 11 are symmetric pairs and likewise 2, 6, 9, & 13).

Table 2 summarizes the results obtained from these different transducers. Similar to the velocity profile results, these measurements indicate that there is no variation in the speed of sound measured by all the transducer pairs which was expected since the fluid tested is homogeneous. However, nonuniformity in concentration of solids in a slurry flow would be detectable using this approach, provided sufficient concentration differences exist.

TABLE 2

Speed of Sound Measurements from Various Transducer Pairs.

| Xducer Pairs | Transit Time ($\mu$s) | Xducer Dist. (mm) | Speed of Sound(m/s) |
|---|---|---|---|
| 4 & 11 | 55 | 81.5 | 1482 |
| 3, 5, 10, & 12 | 53 | 78.5 | 1481 |
| 2, 6, 9, & 13 | 46 | 68.6 | 1491 |
| 1 & 3 | 32 | 47.5 | 1484 |

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of measuring a velocity profile of a fluid flow having an ultrasonic scatterer, the method comprising the steps of:
   (a) providing at least one pair of ultrasonic transducers surrounding said fluid flow;
   (b) measuring a time of flight between said at least one pair of ultrasonic transducers;
   (c) measuring a reflection mode pulsed wideband Doppler between at least one transducer of said at least one pair of ultrasonic tranducers and said ultrasonic scatterer;
   (d) mathematically reconstructing a local speed of sound across a flow section from the time of flight; and
   (e) mathematically reconstructing a local fluid velocity from a combination of the local speed of sound and the reflection mode pulsed wideband Doppler, thereby obtaining the velocity profile.

2. The method as recited in claim 1, further using a plurality of ultrasonic cycles in said step of measuring of a reflection mode pulsed wideband Doppler.

3. The method as recited in claim 2, further providing 5 to 20 pulses of said plurality of ultrasonic cycles.

4. The method as recited in claim 1, further varying a density of said ultrasonic scatterer.

5. An apparatus for measuring a velocity profile of a fluid flow having an ultrasonic scatterer, the apparatus comprising:
   (a) at least one pair of ultrasonic transducers surrounding said fluid flow, said at least one pair of ultrasonic transducers used in measuring a time of flight between said at least one pair of ultrasonic transducers, and a reflection mode pulsed wideband Doppler being measured between at least one transducer of said at least one pair of ultrasonic transducers and said ultrasonic scatterer; and
   (b) an ultrasonic Doppler computer data collection system connected to said at least one pair of ultrasonic transducers, said ultrasonic Doppler computer data collection system including a computer system, said computer system having a first instruction set for mathematically reconstructing a local speed of sound across a flow section from the time of flight, and having a second instruction set for mathematically reconstructing a local fluid velocity from a combination of the local speed of sound and the reflection mode pulsed wideband Doppler, thereby obtaining the velocity profile.

6. The apparatus as recited in claim 5, wherein said ultrasonic Doppler computer data collection system includes a transceiver coupled between said at least one pair of ultrasonic transducers and the computer system, said transceiver transmitting a plurality of ultrasonic cycles.

7. The apparatus as recited in claim 6, wherein said plurality of ultrasonic cycles is from 5 to 20 pulses.

8. The apparatus as recited in claim 5, wherein said ultrasonic scatterer is a variation in density.

* * * * *